(12) United States Patent
Bambeck (10) Patent No.: US 7,414,726 B1
(45) Date of Patent: Aug. 19, 2008

(54) GAS ANALYZER SYSTEMS AND METHODS

(76) Inventor: Robert J. Bambeck, 1921 E. Carnegie Ave., Newport Beach, CA (US) 92705

( * ) Notice: Subject to any disclaimer, the term of this patent is extended or adjusted under 35 U.S.C. 154(b) by 0 days.

(21) Appl. No.: 11/932,464

(22) Filed: Oct. 31, 2007

(51) Int. Cl.
   *G01N 21/00* (2006.01)
(52) U.S. Cl. ...................... 356/436; 356/432
(58) Field of Classification Search .......... 356/432–444
   See application file for complete search history.

(56) References Cited

U.S. PATENT DOCUMENTS

| | | | | |
|---|---|---|---|---|
| 3,885,540 A | * | 5/1975 | Stadler | 123/698 |
| 3,887,473 A | * | 6/1975 | Sternberg et al. | 250/345 |
| 4,043,305 A | * | 8/1977 | Henault | 123/698 |
| 4,168,683 A | * | 9/1979 | Hata et al. | 123/704 |
| 4,224,113 A | * | 9/1980 | Kimura et al. | 205/784.5 |
| 4,471,220 A | * | 9/1984 | Perry et al. | 250/339.04 |
| 4,732,476 A | | 3/1988 | Barshad | |
| 4,993,386 A | * | 2/1991 | Ozasa et al. | 123/25 J |
| 6,151,952 A | * | 11/2000 | Mathews et al. | 73/23.31 |
| 6,382,014 B1 | * | 5/2002 | Breton | 73/23.31 |
| 6,748,004 B2 | * | 6/2004 | Jepson | 373/8 |
| 2006/0236752 A1 | * | 10/2006 | Nakamura | 73/23.21 |

FOREIGN PATENT DOCUMENTS

WO    WO/87/07093    11/1987

OTHER PUBLICATIONS

J.C. Wyant, "Rotating Diffraction Grating Laser Beam Scanner," Applied Optics, vol. 14, No. 5, pp. 1057-1058, May 1975, University of Arizona.
E. Normand et al., "Fast, real-time spectrometer based on a pulsed quantum-cascade laser," Optics Letters, vol. 28, No. 1, pp. 16-18, Jan. 1, 2003.
R. Jiminez et al., "Ozone detection by differential absorption spectroscopy at ambient pressure with a 9.6 um pulsed quantum-cascade laser," Applied Physics B, 2003.
Claire Gmachl et al., "Quantum cascade lasers shape up for trace-gas sensing," Laser Focus World, 5 pages, vol. 43, Issue 10, Sep. 2001.
Bell Laboratories, Physical Sciences Research, Quantum Cascade Lasers, back to Science—applications, 1 page, 2000, http://www.bell-labs.com/org/physicalsciences/projects/q.
Bambeck Systems Inc., brochure, "CO-3000 Series, Combustion Efficiency Systems," 5th Edition, 1993.

* cited by examiner

*Primary Examiner*—L. G. Lauchman
*Assistant Examiner*—Jarreas C Underwood
(74) *Attorney, Agent, or Firm*—Larry K. Roberts (57) ABSTRACT

A method and system for analyzing gases is described. An exemplary embodiment measures flue gas in a stationary industrial process heater or boiler installation in which fuel is burned. Another exemplary embodiment provides an equivalent oxygen concentration analyzer.

23 Claims, 7 Drawing Sheets

Equivalent O₂ Analyzer Look-up Table

| | C | H | O | N | Flue Gas Molecules Moles Volume | Stoichiometric Flue Gas Concentrations % $CO_2$ | | % $H_2O$ | C:H Ratio | Measured $CO_2$ | Dilution Excess Air | Flue Gas $O_2$ |
|---|---|---|---|---|---|---|---|---|---|---|---|---|
| Methane $C_1H_4$ | + | $2O_2$ | + | $8N_2$ = $1CO_2$ + $2H_2O$ + $8N_2$ | 11 | 9.09% | 1 | 18.18% 2 | 0.500 | 8.00% | 13.64% | 2.50% |
| Ethane $C_2H_6$ | + | $7O_2$ | + | $28N_2$ = $4CO_2$ + $6H_2O$ + $28N_2$ | 38 | 10.53% | 4 | 15.79% 6 | 0.667 | 8.00% | 31.58% | 4.99% |
| Propane $C_3H_8$ | + | $5O_2$ | + | $20N_2$ = $3CO_2$ + $4H_2O$ + $20N_2$ | 27 | 11.11% | 3 | 14.81% 4 | 0.750 | 8.00% | 33.89% | 5.82% |
| Butane $C_4H_{10}$ | + | $13O_2$ | + | $52N_2$ = $8CO_2$ + $10H_2O$ + $52N_2$ | 70 | 11.43% | 8 | 14.29% 10 | 0.800 | 8.00% | 42.86% | 6.24% |
| Ethylene $C_2H_4$ | + | $6O_2$ | + | $24N_2$ = $4CO_2$ + $4H_2O$ + $24N_2$ | 32 | 12.50% | 4 | 12.50% 4 | 1.000 | 8.00% | 56.25% | 7.49% |

Compare $CO_2$ measurement with Stoichiometric $CO_2$ for given C-H ratio

GAS ANALYZER SYSTEMS AND METHODS

BACKGROUND

An exemplary application for the systems and methods described herein is as a gas analyzer for determining combustion flue gas oxygen concentrations in stationary sources such as large process heaters and industrial boilers.

In the past, combustion flue gas has been measured directly with a Zirconium Oxide or other type analyzer for determining excess air remaining in the flue gas, to ensure that enough air is present for stoichiometric combustion.

DETAILED DESCRIPTION

In the following detailed description and in the several figures of the drawing, like elements are identified with like reference numerals. The figures are not to scale, and relative feature sizes may be exaggerated for illustrative purposes.

Figure 1:
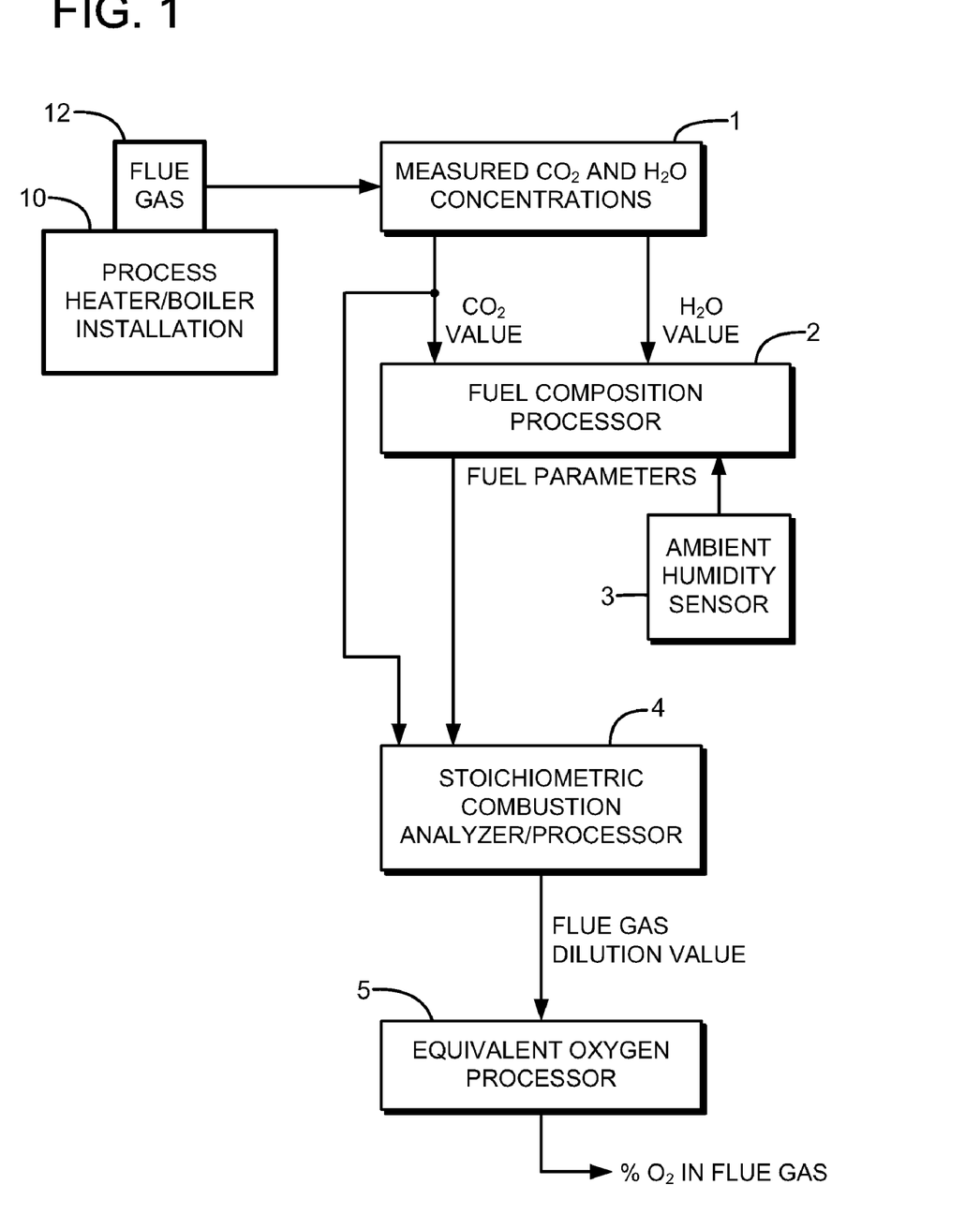
FIG. 1 is a diagrammatic schematic block diagram of an exemplary embodiment of a system for determining an oxygen concentration in flue gases of a process heater or boiler installation.

An exemplary embodiment of a gas analyzer system is depicted in schematic form in FIG. 1. This embodiment provides an equivalent diatomic oxygen $O_2$ analyzer system, which measures $CO_2$ and water vapor ($H_2O$) in the combustion flue gas across the furnace, stack or flue duct 12 of a process heater or boiler installation 10 with a light source, e.g., a Quantum Cascade (QC) laser. The system processes the measurement signals to determine the oxygen dilution (relative to a stoichiometric concentration) and thus excess $O_2$ in the flue gas. The dilution can only be caused by air which is about 21% $O_2$ by volume concentration in the ambient, ground level earth atmosphere.

The constituents of the fuel are primarily hydrogen and carbon. Any other constituents in the flue gas (i.e. NOx, CO, $SO_2$ and inert gases) will be insignificant in comparison to the by-products of combustion $CO_2$ and $H_2O$ when determining the dilution.

Measurement of $CO_2$ and $H_2O$ concentrations 1 in combustion flue gas can be used to determine the hydrogen to carbon ratio of the fuel being burned since the preponderance of the composition of fuel burned is hydrogen and carbon.

Only air is added to the fuel in the process heater or boiler installation to produce combustion. The earth's air is composed by volume concentration of 21% oxygen, 78% nitrogen, with the remainder inert gases which are insignificant for purposes of this analysis and for the determination of the equivalent $O_2$. Flue gas dilution is assumed to be caused by excess air beyond that needed for complete combustion.

By ratioing the flue gas measurements of $CO_2$ and $H_2O$, the molar composition of the fuel can be determined. Since the ratio does not change no matter what the dilution is, the C to H ratio determines the fuel composition. Dilution is the variance from the $CO_2$ stoichiometric combustion mixture.

A correction may be made for the affect of the relative humidity change and thus the water vapor content change in the ambient air. To accomplish this, an industrial quality, commercially available humidity analyzer may be added to the system in locations where the relative humidity changes significantly. The signal from this analyzer is added as a correction to the $H_2O$ measurement.

The stoichiometric combustion general equation ($C_mH_n + (m+n/4)O_2 + 2N_2 = mCO_2 + n/2H_2O + 10n/2N_2$) can be used to determine the moles of $CO_2$ that should be present in the flue gas under stoichiometric conditions with the measured $CO_2$ and $H_2O$ values. In an exemplary embodiment in which the fuel is methane, then the stoichiometric combustion equation is $CH_4 + 2O_2 + 8N_2 = CO_2 + 2H_2O + 8N_2$), The stoichiometric combustion condition is the condition in which only the exact amount of air is present to burn any given fuel with no molecules remaining of air or fuel. The percentage by volume of $CO_2$ that should be in the flue gas under stoichiometric conditions can be determined by applying Charles' ideal gas law equation PV=n RT. This will produce the stoichiometric percentage by volume $CO_2$ for the particular fuel C:H ratio being burned at any given time. In an exemplary embodiment of an analyzer, the stoichiometric percentages can be pre-calculated and stored in a look-up table in the memory of the analyzer system.

The flue gas percentage by volume of $CO_2$ measured by the analyzer system is then compared to the calculated stoichiometric percentage by volume $CO_2$ and the ratio will be the flue gas % dilution. This dilution of the flue gas is the variance of the measured percentage from the stoichiometric percentage.

Any significant dilution can only be caused by excess air.

Knowing the excess air, the percentage oxygen (% $O_2$) in the flue gas may be calculated through the equation:

$$\% O_2 = (\% \text{ excess air} \times 21)/(1+\text{excess air})$$

Referring again to FIG. 1, the process heater or boiler installation 10 includes a flue or duct 12 through which combustion flue gases pass. The analyzer system measures the $CO_2$ and $H_2O$ concentrations 1 in the flue gas, and these concentration values are processed by a fuel composition processor 2 to determine the parameters of the fuel being burned. The processor 2 may compensate for the ambient humidity which is sensed by sensor 3, although this is an optional feature for some installations. The fuel parameters and the $CO_2$ concentration value are processed by a stoichiometric combustion analyzer 4 to determine a fuel gas dilution value. An equivalent oxygen processor 5 calculates the percentage oxygen in the flue gas from the dilution level.

Figure 2:
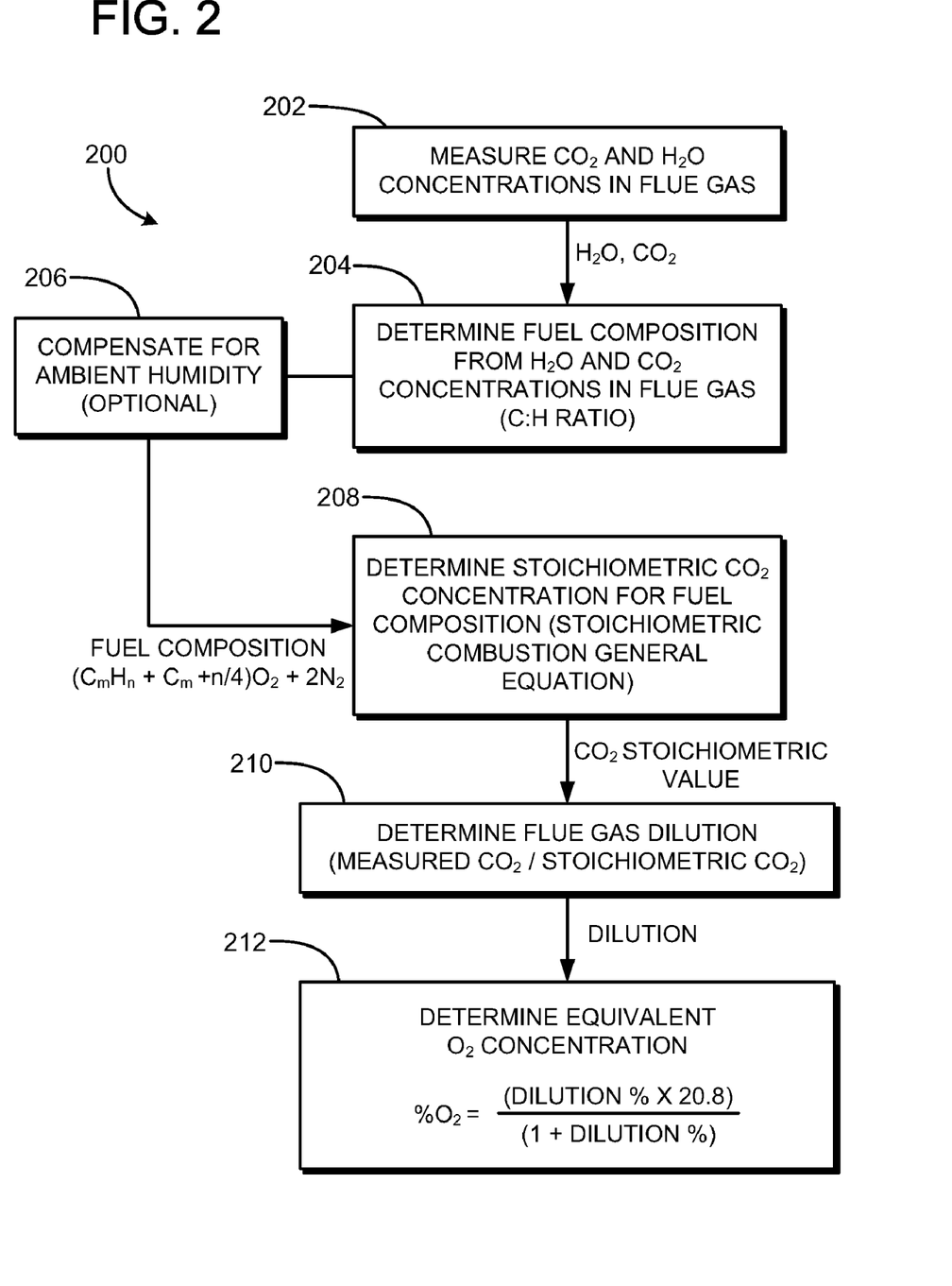
FIG. 2 is a process flow diagram illustrating an exemplary process for determining an equivalent oxygen concentration in flue gases.

FIG. 2 is a flow diagram illustrating an exemplary method 200 for determining an oxygen concentration in flue gas of a process installation, for example, a system as depicted in FIG. 1. At 202, concentrations of $CO_2$ and $H_2O$ in the flue gas are measured. A fuel composition is determined at 204 from these measured as the C:H ratio. The fuel composition determination may optionally be compensated for the ambient humidity at 206. The stoichiometric $CO_2$ concentration may be determined or calculated at 208, using the stoichiometric combustion general equation set out above. From this value, the flue gas dilution may be calculated at 210, as the ratio of the measured $CO_2$ value and the stoichiometric value. The oxygen concentration corresponding to the dilution may then be calculated at 212.

Figure 3:
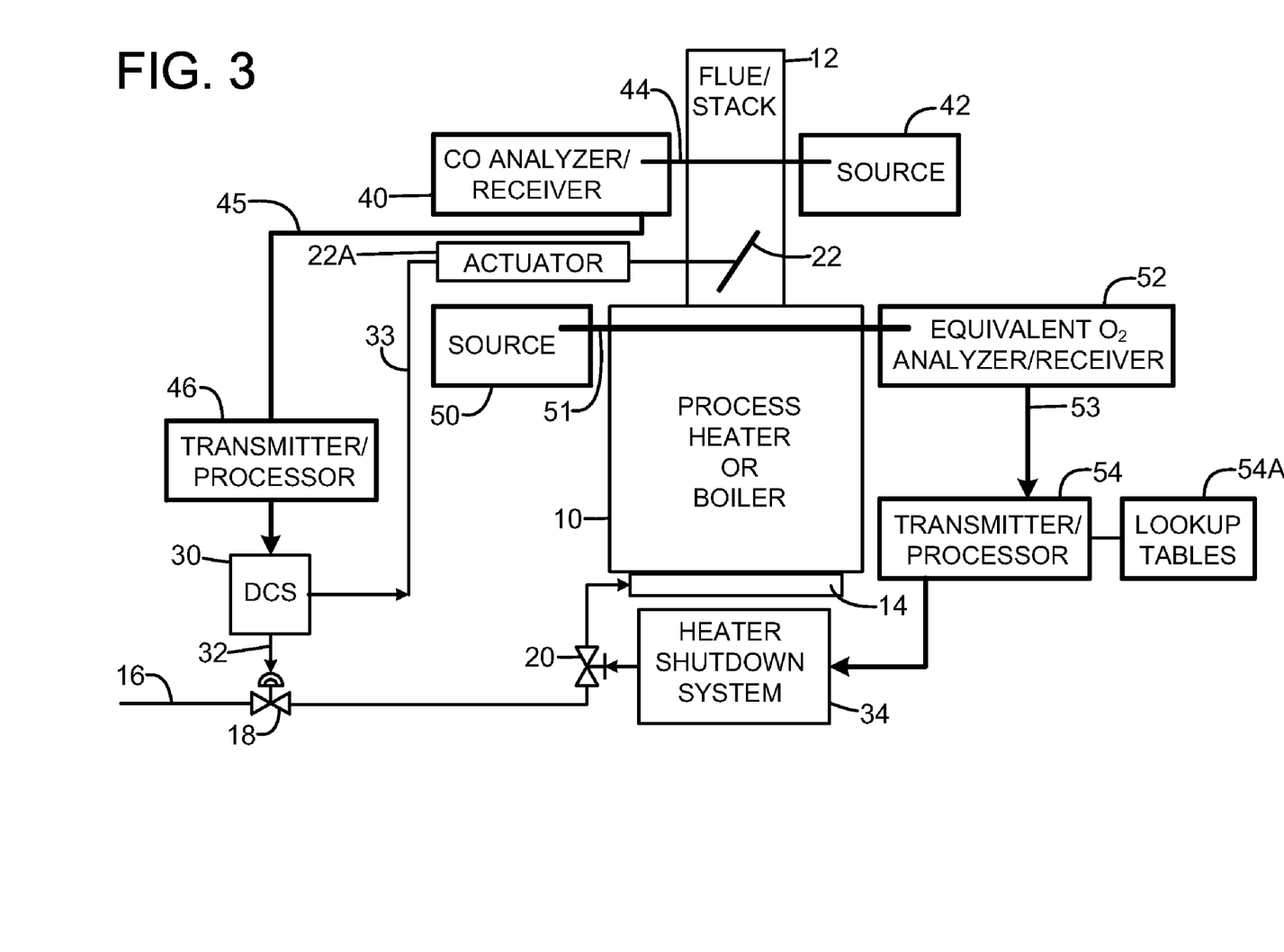
FIG. 3 is a schematic block diagram of an exemplary embodiment of an oxygen analyzer system employed in an exemplary process heater or boiler system.

An exemplary embodiment of an analyzer system may be implemented in a combustion air control system for efficient low excess air control or heater safety shutdown systems, e.g. as part of the safety instrumented system. FIG. 3 is a schematic block diagram of an exemplary embodiment of a control system for a process heater or boiler installation. The control system employs an equivalent $O_2$ analyzer interfaced with a safety system.

FIG. 3 depicts a process heater or boiler 10, with an exhaust flue or stack 12. The process heater or boiler 10 may be installed, for example, in an oil refinery installation, chemical plant, paper mill boiler plant, university or hospital central power boiler plant or any steam producing power plant, by way of example only. A burner system 14 is fed by a fuel gas or liquid through a feed line 16. The flow of fuel through the line is controlled by control valve 18. A computer-based distributed control system (DCS) 30 in turn controls the valve 18 by an electrical valve control signal applied on control link or line 32. In an exemplary embodiment, the control valve 18 is configured to modulate the flow of fuel gas in dependence on the electrical control signal provided by the DCS 30.

A movable damper 22 is mounted in the flue duct or stack 12, and includes a pneumatic damper actuator to control the air flow through the system 10 and flue duct or stack 12. The DCS 30 provides a damper control signal on line 33 to the damper actuator of the damper 22.

The carbon monoxide (CO) concentration in the flue gas is monitored by a CO analyzer/receiver 40 mounted on one side of the flue or stack, which receives an analyzer radiation beam 44 generated by source 42 mounted on an opposite side of the flue or stack. The beam 44 passes through the flue gas, and is detected by the CO analyzer/receiver 40, which provides a CO data signal to the transmitter/processor 46. The transmitter/processor in turn processes the CO data signal to determine a CO concentration level in the flue gas, and provides a CO concentration signal to the DCS 30. In an exemplary embodiment, the source 42 is a quantum cascade (QC) laser system which generates a laser beam 44 at a center wavelength of 4.7 um. The laser system output beam wavelength may be tunable over a range between 4.5 um and 4.9 um, in one exemplary embodiment. The receiver detects the intensity of the absorption wavelength range and determines the concentration of CO. A QC laser system is used in an exemplary embodiment of the CO analyzer because it is able to generate relatively high energy, and its output can be swept over the absorption bandwidth of CO. It also allows for the detection of the overlapping wavelengths of $H_2O$ and $CO_2$ in this region.

Figure 6:
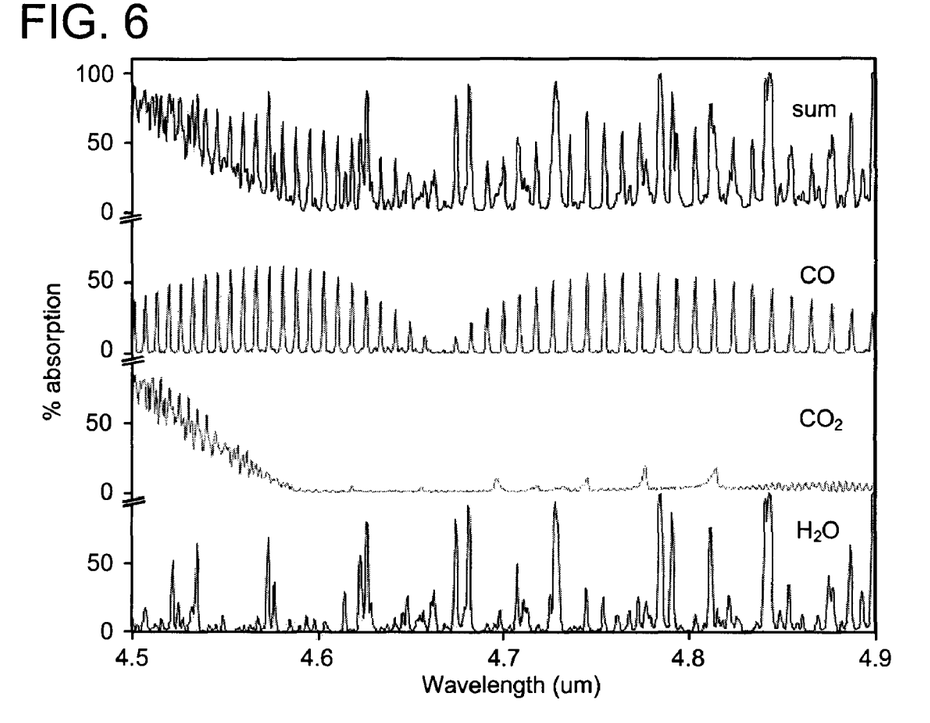
FIG. 6 graphically illustrates the absorption characteristic and signature wavelengths of the combustion gases to be measured by an exemplary system.

In an exemplary embodiment, the analyzer/receiver 40 and the transmitter/processor 46 may be adapted to determine the CO concentration by utilizing the signature wavelengths of the absorption characteristics of CO. FIG. 6 depicts the % absorption of CO as a function of wavelength. It may be seen that the CO absorption characteristic has a number of peaks in the wavelength range between 4.5 um and 4.9 um. The analyzer/receiver 40 can be adapted to take a number of measurements, say ten, on or surrounding each of the absorption peak wavelengths as the light source is swept through the wavelength range. Thus, for example, the time varying output of the detector comprising the analyzer/receiver 40 is related to the wavelength being transmitted through the flue gas as the wavelength is swept through the wavelength range of interest, so that the intensity value measured by the analyzer/receiver 40 at a given instant of time is correlated to the wavelength transmitted through the flue gas at that time instant. With a plurality of measurements at each peak, the measurements can be processed to form an average intensity value at each peak wavelength, and these average values can in turn be processed with knowledge of the signature wavelengths of CO to provide a CO concentration. Because the absorption peaks for CO, $CO_2$ and H2O occur at mutually distinct wavelengths, as illustrated in FIG. 6, the concentrations of these three gases may be determined using the same analyzer light source and detector system.

An exemplary embodiment of the analyzer light source 42 is a quantum cascade (QC) laser system. The QC laser may be adapted to generate a relatively broad spectrum of energy over a wavelength range of interest, e.g. for this application in a range of about 4.5 um to about 4.9 um. A QC laser is preferred for an exemplary application over a diode laser because it may be adapted to produce a much higher intensity output beam Preferably the QC laser system is operable at room temperatures, without active or cryogenic cooling requirements. The laser system may be operated in a pulsed mode of operation, for example, 50,000 pulses per second in one example. The laser system may be adapted to sweep the output beam through the wavelength range of interest, in this case between about 4.5 um to about 4.9 um, in a sweep period, which for one exemplary embodiment may be one millisecond. There are various known techniques for sweeping the output wavelength range, including passing the laser beam through a rotating optical grating.

In an exemplary embodiment, the QC laser system 42 includes output optics which will spread the diameter of the transmitted beam, so that the beam after passing through the flue gas is much larger in diameter than the beam size generated by the laser system. For example, if the laser spot size at the output of the QC laser system is 0.5 inch in diameter, the beam after passing through the flue gas and incident on the detector may be on the order of 1 foot in diameter. This "overfill" of the detector ensures that a portion of the beam is received in the detector, even in the presence of some ambient vibration or movement of the QC laser system and/or the detector system. For example, the detector system may have an active area on the order of 0.25 inch square.

In an exemplary embodiment, the DCS 30 performs a control algorithm, in which the CO concentration signal is a parameter, to control the valve 18 and the damper 22 to control the air fuel operation of the process heater or boiler 10.

The control system depicted in FIG. 3 further includes an equivalent $O_2$ sensor system for detecting an $O_2$ concentration within the heater or boiler furnace or combustion chamber 10, by detecting concentrations of water vapor and carbon dioxide, and using the detected concentrations of these materials to inferentially determine the oxygen concentration. Thus, the sensor system includes a source 50 which generates a radiation beam 51 and directs the beam from one side of the furnace through the combustion gases inside the furnace to an analyzer/receiver 52 on the opposite side of the chamber. In an exemplary embodiment, the source 50 is a QC laser system having the characteristics described above for the CO analyzer light source 42. The laser system 50 may be adapted to sweep the output beam through the wavelength range of interest, in this case between about 4.5 um to about 4.9 um, in a sweep period, which may be one millisecond. The analyzer/receiver 52 includes a detector system to measure the intensity of the specific wavelength as the QC laser system output is swept over the 4.5 um to 4.9 um region. This received energy intensity results in detector signals 53 indicative of the $H_2O$ and $CO_2$ concentrations in the boiler furnace. The oxygen analyzer system further includes a transmitter/processor 54 which uses the detected $H_2O$ and $CO_2$ concentrations to determine the carbon to hydrogen ratio of the fuel. This may be determined by use of a lookup table, in which the detected $H_2O$ and $CO_2$ concentrations are parameters to address precalculated carbon to hydrogen ratios corresponding to these parameters. This ratio in turn is used to determine the air dilution, i.e. the equivalent $O_2$ level, in the furnace.

Figure 4:
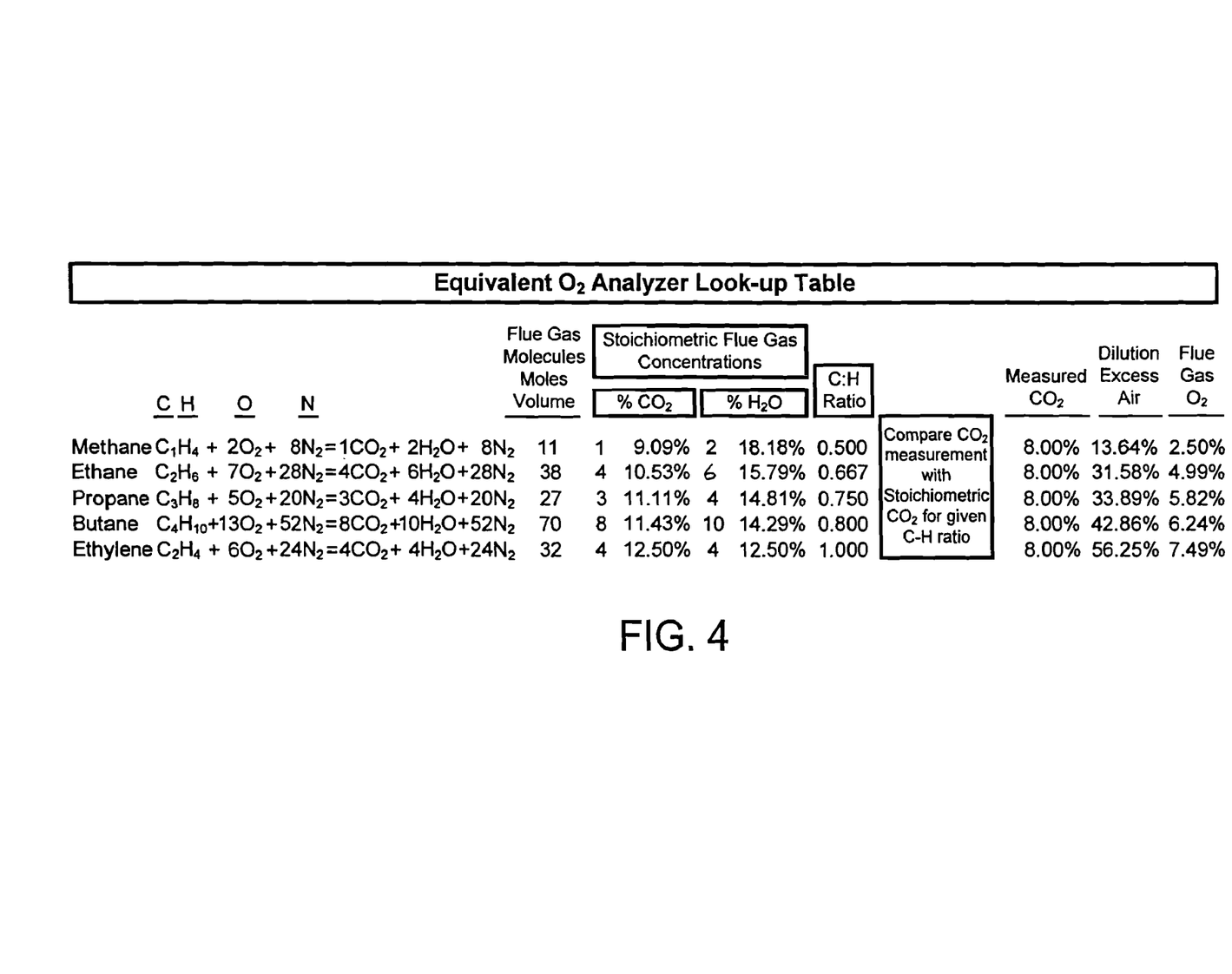
FIG. 4 illustrates an exemplary look up table for an exemplary oxygen analyzer system.

FIG. 4 diagrammatically depicts exemplary values in a look-up table, for several exemplary fuel gases, i.e. Methane, Ethane, Propane, Butane and Ethylene. These are the components of refinery fuels. Most other plants burn 100% Methane typically. Refineries typically have a preponderance of Methane with the other fuels mixed in randomly. The table of FIG. 4 sets out stoichiometric flue gas concentrations for several exemplary $H_2O$ and $CO_2$ concentrations and the corresponding C:H ratios. The oxidation process chemical equation is balanced for complete and perfect combustion. This is known as stoichiometric combustion. The total molecules in the equations are the same as the number of moles and % volume. These are used to calculate the % of $CO_2$ and $H_2O$ in the products of combustion. These % numbers are ratioed to obtain the ratio of carbon to hydrogen. The measured $CO_2$ value is assumed to be 8% in all cases for this exemplary demonstration table. Dilution is calculated by the excess air formula and oxygen is assumed to be 21% of air. The table includes a box "compare $CO_2$ measurement with stoichiometric $CO_2$ for given C:H ratio." In an exemplary embodiment, the comparison is inherent in the lookup table. In typical plant installations, the C—H ratio is variable, since the fuel mixture typically randomly changes with time.

Referring again to FIG. 3, the transmitter/processor 54 generates a dilution or equivalent $O_2$ signal, and in this exemplary embodiment, the signal is provided to the heater shutdown system 34 for the process heater or boiler system. The shutdown system 34 acts under certain conditions to shut off the fuel gas flow to the burner system 14 by turning off the valve 20. In this exemplary embodiment, the shutdown system 34 also is responsive to the air dilution signal from the oxygen analyzer system, and can shut down the heater or boiler system if the air dilution is below some predetermined threshold. The designers of the shutdown system may determine the threshold below which the air dilution, as measured by excess oxygen, available is to close to starving the combustion, leading to a fuel rich, explosive condition, and use this measurement to cut fuel to low fire or shut down the heater.

Figure 5:
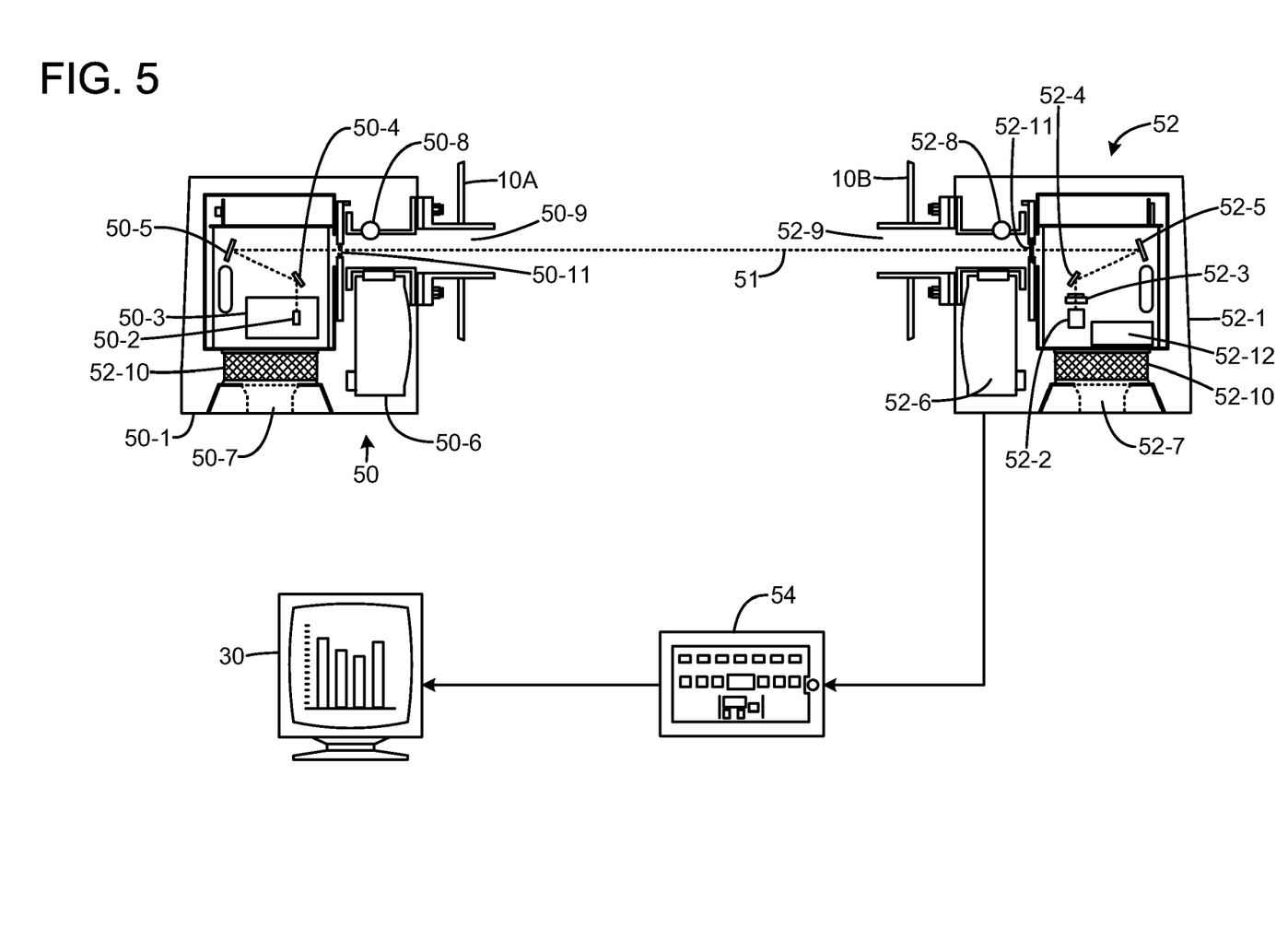
FIG. 5 is a schematic block diagram of an exemplary embodiment of an equivalent oxygen analyzer system and application.

An exemplary embodiment of a source 50 and an analyzer/receiver 52 is diagrammatically illustrated in FIG. 5. For this example, the analyzer is shown interfaced with a refinery or plant Distributed Control System (DCS). The source 50 includes a housing 50-1 mounted to a port 50-9 in the duct wall 10A. Within the housing 50-1 is mounted a semiconductor QC laser 50-2, with its power supply 50-3. The laser generates a beam 51 which is directed by mirrors 50-4 and 50-5 through a slide-mounted window 50-11, through port 50-9 through the process heater or boiler. The QC laser system sweeps or scans a wavelength range around the center wavelength of 4.7 um. In an exemplary embodiment, the sweep period through the wavelength range is one millisecond, and is selected so as to be fast enough so as not to be affected by process gas variations. The sweep repetition rate is preferably selected to be fast enough so as not to be affected by combustion variations. In one exemplary embodiment, the sweep repetition rate is 10 sweeps per second. A blower 50-6 draws air into the housing through air inlet 50-7 and filter 50-10, and an air purge sensor 50-8 detects if a purge exists. The purge isolates the analyzer at the window from the flue gas and thus defines a measurement path length. The analyzer enclosure is completely sealed with only the laser beam transmitting through the window.

Still referring to FIG. 5, the analyzer receiver system 52 includes analogous elements to those of the source 50, including a housing 52-1 mounted to a port 52-9 in the duct wall 10B. Within the housing 52-1 is mounted a detector 52-2, and a calibration cell 52-3. The laser beam 51 enters the system 52 through a slide-mounted window 52-11 and is directed by mirrors 52-4 and 52-5 to the detector. The calibration cell has a known amount of gas in it or an equivalent optical filter for a standard concentration value. It inserts into the laser beam when the analyzer is to be span calibrated. Span Calibration is the up-range level check (usually approx. 70% of full scale). This shows how much the analyzer reacts to a gas that is being placed in the measurement beam and determines if the analyzer is calibrated to react properly. A blower 52-6 draws air into the housing through air inlet 52-7 and filter 52-10, and an air purge sensor 52-8 detects if a purge exists. The purge isolates the analyzer at the window from the flue gas and thus defines a measurement path length. The analyzer enclosure is completely sealed with only the laser beam transmitting through the window. The system 52 further includes a signal transmitter which generates the detector data signals which are passed to the transmitter/processor 54.

In an exemplary embodiment, the transmitter/processor 54 uses curve fitting algorithms with the spectral scan produced by the QC laser 50-2 to separate out the measurements for the individual gases ($CO_2$ and $H_2O$) and the detector 52-2, and develops $H_2O$ % and $CO_2$% by volume concentrations. A lookup table is used for the path-length, flue gas temperature and absolute pressure. The detector 52-2 output may be processed to count the number of molecules it sees. Path length, temperature and pressure are needed to determine the volumetric concentration from this molecule count. The volumetric values are required to determine the C—H ratio and thus the dilution.

FIG. 6 illustrates signature wavelengths (% absorption as a function of wavelength) of exemplary combustion gases (CO, $CO_2$ and $H_2O$) to be measured by a system illustrated in FIG. 3, for example, as well as the sum of the signature wavelengths. The sum is what the detector actually sees after the laser beam is transmitted through the flue gas. The signature wavelengths are superimposed over the sum to distinguish which wavelengths are from the particular species of concern.

Alternate methods for accomplishing the dilution measurement of the flue gas and thus the % excess air ($O_2$) include:

a. Measure $CO_2$ and $H_2O$ with 2 diode lasers since a diode laser measure a single species. This may result in a higher cost then a single QC laser.

b. Measure $CO_2$ and $H_2O$ with an IR light beam across-stack analyzer.

This may result in a higher cost than a single QC laser.

With these measurements the look-up table can be placed in an industrial process computer and the equivalent $O_2$ can be derived.

An equivalent $O_2$ analyzer system provides a very advantageous method to measure appropriate gases for combustion control and not be concerned with the high concentration of $O_2$ in the air overwhelming a direct $O_2$ analyzer. This is a significant problem with conventional technology. The analyzer system may be applied to a combustion control system (as illustrated in FIG. 5) or to a safety shutdown system (as illustrated in FIG. 3).

An exemplary embodiment of an equivalent $O_2$ analyzer thus:
a. measures $CO_2$ and $H_2O$,
b. with a single QC laser light beam,
c. continuously across the stack, furnace or flue duct,
d. with less than one/tenth of a second updates by rapid sweeping the wavelength range with a rotating optical grating before transmitting the laser beam.

The equivalent $O_2$ analyzer provides an excellent way to infer and extrapolate an equivalent $O_2$ measurement across the flue gas of a fired process heater or industrial boiler.

Figure 7A:
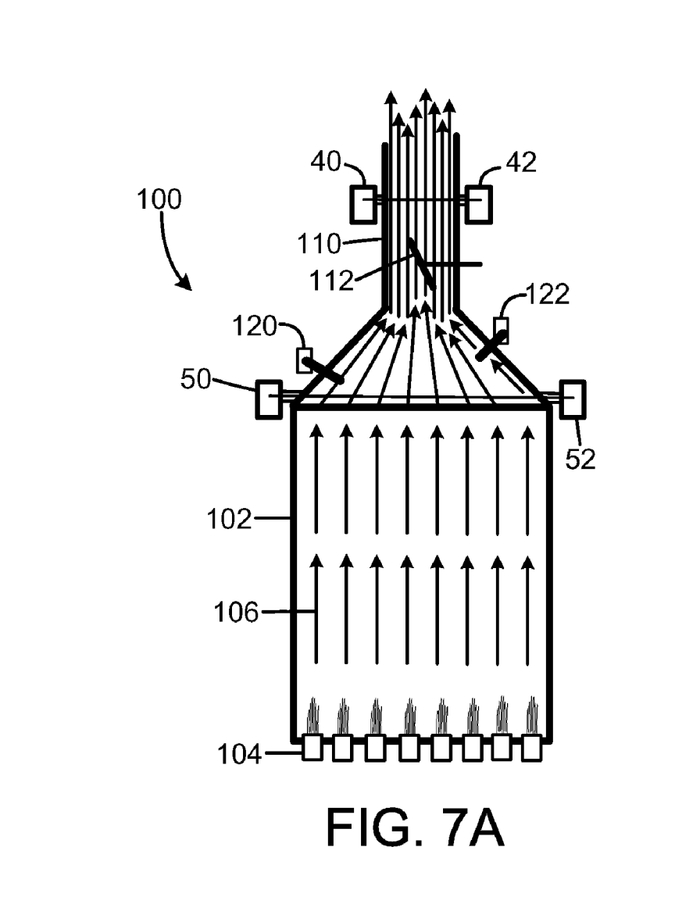
FIG. 7A diagrammatically depicts a combustion gas analyzer system for a process heater application.
Figure 7B:
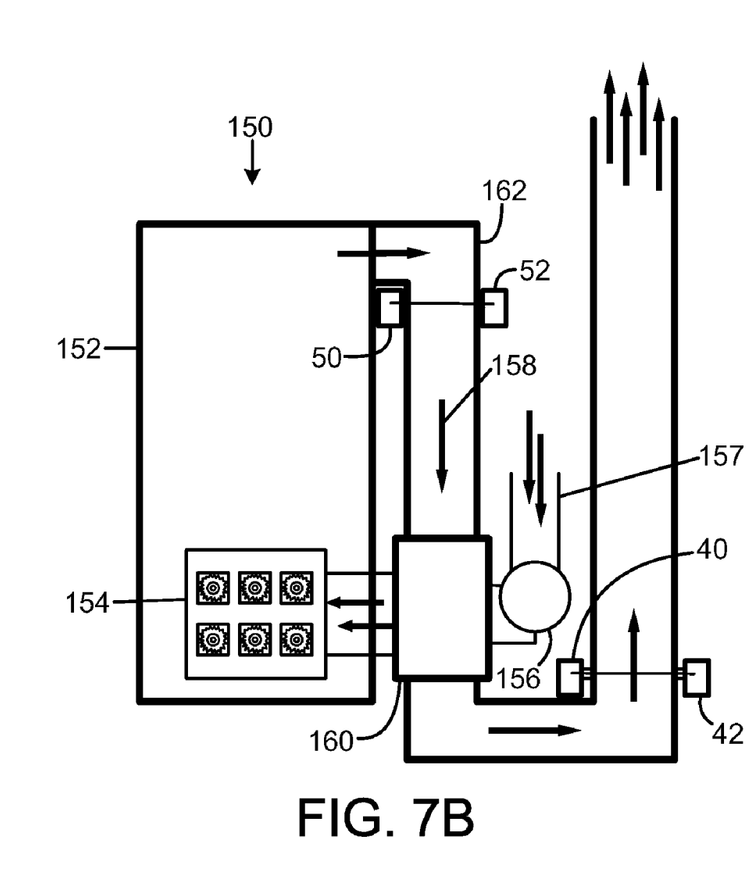
FIG. 7B diagrammatically depicts a combustion gas analyzer system for a boiler application.

FIGS. 7A and 7B illustrate exemplary configurations of respective process heater and boiler installations 100 and 150. FIG. 7A depicts an exemplary process heater system 102, with multiple burners 104 for burning a fuel gas. The process heater system includes a flue or stack 110 in which a flue damper 112 is positioned. Air flow within the heater system is depicted by arrows 106. A CO analyzer including a QC laser source 40 and an analyzer/receiver 42 are positioned on opposite sides of the flue 110, similar to the arrangement depicted in FIG. 3. The system 100 may also include a draft pressure transmitter 120 and an oxygen analyzer 122. The analyzer 122 may be a system which directly measures $O_2$, e.g. a Zirconium Oxide analyzer. The system also includes an equivalent oxygen analyzer including QC laser source 50 and analyzer/receiver 52, as described above regarding the embodiments of FIGS. 3 and 5. For some installations, the analyzer 122 may be omitted, and its function replaced by the equivalent oxygen analyzer.

FIG. 7B illustrates an exemplary boiler installation, which includes the boiler 152, burners 154, an air intake flue 157 and a forced draft fan 156 which delivers air through a preheater 160 to the boiler burner unit 154. Exhaust air is passed out flue 162, as indicated by arrows 158. A CO analyzer including a QC laser source 40 and an analyzer/receiver 42 are positioned on opposite sides of the flue 162 downstream of the preheater 156, similar to the arrangement depicted in FIG. 3. The system also includes an equivalent oxygen analyzer including QC laser source 50 and analyzer/receiver 52, as described above regarding the embodiments of FIGS. 3 and 5. In this installation, the equivalent oxygen analyzer is positioned upstream of the preheater at the output of the boiler.

Although the foregoing has been a description and illustration of specific embodiments of the subject matter, various modifications and changes thereto can be made by persons skilled in the art without departing from the scope and spirit of the invention as defined by the following claims.

What is claimed is:

1. A method for analyzing flue gas in a stationary industrial process heater or boiler installation in which fuel is burned, comprising:
   measuring concentrations of carbon dioxide ($CO_2$) and water vapor ($H_2O$) in the flue gas;
   determining fuel composition parameters from said measured concentrations of $CO_2$ and $H_2O$ in the flue gas;
   determining a stoichiometric $CO_2$ concentration corresponding to the fuel composition parameters;
   determining a flue gas dilution based on said measured $CO_2$ concentration and said stoichiometric $CO_2$ concentration.

2. The method of claim 1, further comprising:
   determining an equivalent oxygen concentration in said flue gas using said flue gas dilution.

3. The method of claim 1, wherein said measuring concentrations of $CO_2$ and $H_2O$ is performed by directing a laser beam generated by a quantum cascade laser through the flue gas to a detector, and sweeping the beam over a wavelength range centered at around 4.7 um.

4. The method of claim 1, wherein said determining fuel composition comprises determining a carbon:hydrogen ratio in said flue gas.

5. The method of claim 4, wherein said determining a stoichiometric $CO_2$ concentration corresponding to the fuel composition parameters comprises:
   using a stoichiometric combustion general equation and said C:H ratio to determine the fuel composition.

6. The method of claim 1, wherein said determining a stoichiometric $CO_2$ concentration corresponding to the fuel composition parameters comprises:
   calculating the concentration using a stoichiometric combustion general equation.

7. The method of claim 1, wherein said determining a stoichiometric $CO_2$ concentration corresponding to the fuel composition parameters comprises:
   using the measured concentrations of $CO_2$ and $H_2O$ in the flue gas to address pre-calculated corresponding stoichiometric $CO_2$ concentration values in a stored look-up table in an electronic memory.

8. An equivalent oxygen analyzer system for analyzing flue gas in a stationary industrial process heater or boiler installation in which fuel is burned, comprising:
   a detector system for measuring concentrations of carbon dioxide ($CO_2$) and water vapor ($H_2O$) in the flue gas, said system including a light source for generating a light beam in a wavelength range;
   an analyzer system for determining fuel composition parameters of the burned fuel from said measured concentrations of $CO_2$ and $H_2O$ in the flue gas and determining a stoichiometric $CO_2$ concentration corresponding to the fuel composition parameters, said analyzer system further adapted to determine an equivalent oxygen concentration in said flue gas using said measured concentrations of $CO_2$ and $H_2O$ in the flue gas and said stoichiometric $CO_2$ concentration.

9. The system of claim 8, wherein said analyzer system includes an electronic memory storing a look up table of flue gas dilution values corresponding to a set of said measured concentrations of $CO_2$ and $H_2O$ in the flue gas.

10. The system of claim 8, wherein said analyzer system is adapted to determine a flue gas dilution based on said measured $CO_2$ concentration and said stoichiometric $CO_2$ concentration, and to determine said equivalent oxygen concentration using said dilution.

11. The system of claim 8, wherein said light source includes a quantum cascade laser system.

12. The system of claim 11, wherein the quantum cascade laser system is adapted to sweep a wavelength range from about 4.5 um to about 4.9 um.

13. The system of claim 12, wherein the quantum cascade laser system is operable in a pulsed mode.

14. The system of claim 8, further including:
   a detector system for measuring concentrations of carbon monoxide (CO) in the flue gas, said system including a light source for generating a light beam in a wavelength range, said light source including a quantum cascade laser.

15. A gas analyzer system for analyzing gas produced in a stationary industrial process heater or boiler installation in which fuel is burned, comprising:
   a light system for directing a light beam through the gas, said light beam swept through a wavelength range between about 4.5 um and 4.9 um during a sweep period;
   said light system including a quantum cascade laser;

a detector system arranged to receive the light beam after it has passed through the gas, the detector system including a detector sensitive to light in said wavelength range and producing a detector output signal indicative of light intensity of the received light beam;

an analyzer system responsive to the detector output signal to determine a measured concentration of at least one gas component of the gas component of the gas;

wherein said at least one gas component includes carbon dioxide and water vapor, and said analyzer system is further adapted to determine an oxygen dilution value using determined concentrations of carbon dioxide and water vapor.

16. The system of claim 15, wherein the light beam is directed through gas within a boiler chamber of a boiler installation.

17. The system of claim 16, wherein said gas component is one of carbon dioxide and water vapor.

18. The system of claim 15, wherein the analyzer system is further adapted to determine an equivalent diatomic oxygen concentration.

19. The system of claim 15, wherein the light beam is directed through flue gas passing through an output flue of the heater or boiler installation.

20. The system of claim 19, wherein the gas component is carbon monoxide.

21. The system of claim 15, wherein the gas component is one of carbon monoxide, carbon dioxide and water vapor.

22. A method for determining an equivalent oxygen concentration, comprising:

measuring $CO_2$ and $H_2O$ concentrations in gas produced by a stationary industrial process heater or boiler installation in which fuel is burned, said measuring performed with a light beam generated by a single quantum cascade laser across a stack, furnace or flue duct of the installation, and wherein the wavelength of the beam is swept through a wavelength range in a sweep period less than one second;

determining a dilution value of the gas from said measured $CO_2$ and $H_2O$ concentrations;

determining an equivalent oxygen concentration from said dilution value.

23. The method of claim 22, wherein said wavelength range is from about 4.5 um to about 4.9 um.

* * * * *